US009863855B2

(12) United States Patent
Arimoto

(10) Patent No.: US 9,863,855 B2
(45) Date of Patent: Jan. 9, 2018

(54) APPARATUS AND METHOD FOR OBTAINING LIQUID SAMPLE FROM GASEOUS SAMPLE

(71) Applicant: Panasonic Intellectual Property Management Co., Ltd., Osaka (JP)

(72) Inventor: Satoshi Arimoto, Shiga (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 361 days.

(21) Appl. No.: 14/740,141

(22) Filed: Jun. 15, 2015

(65) Prior Publication Data
US 2016/0238492 A1    Aug. 18, 2016

(30) Foreign Application Priority Data
Feb. 13, 2015   (JP) .................. 2015-025966

(51) Int. Cl.
*G01N 1/22*          (2006.01)
*G01N 33/497*        (2006.01)
(Continued)

(52) U.S. Cl.
CPC ......... *G01N 1/2202* (2013.01); *B05B 5/0255* (2013.01); *B05B 5/0535* (2013.01);
(Continued)

(58) Field of Classification Search
CPC ......... G01N 1/2202; G01N 2001/2223; G01N 33/497; G01N 33/4972; G01N 2001/2282; G01N 1/2273; G01N 2001/2244; B05B 5/0255; B05B 5/0535; B05B 5/16

USPC ........... 73/863.21, 23.2, 23.3, 53.01, 61.43, 73/64.56, 863, 863.11, 863.12, 864.81, 73/865.5; 239/690, 690.1, 128; 422/84
See application file for complete search history.

(56) References Cited

U.S. PATENT DOCUMENTS 7,972,277 B2      7/2011   Oki et al.
8,056,395 B2 *   11/2011   Oki .................. B03C 3/014
                                              73/23.3

FOREIGN PATENT DOCUMENTS

JP       4-325080       11/1992
JP       2007-333570    12/2007
(Continued)

*Primary Examiner* — Robert R Raevis
(74) *Attorney, Agent, or Firm* — McDermott Will & Emery LLP

(57) ABSTRACT

The present invention provides an electrostatic atomizer comprising: a container having an inlet; an atomization electrode having one end projecting in the container; an opposite electrode provided in the container; a tubular collection electrode provided opposite to the atomization electrode; a mask surrounding an outer periphery of the tubular collection electrode; and a cooling part for cooling the tubular collection electrode. The opposite electrode is provided between the atomization electrode and the tubular collection electrode. The mask is formed of resin. The mask comprises a mask through-hole. The tubular collection electrode is inserted in the mask through-hole. One end of the tubular collection electrode is located in the mask through-hole. The present invention provides a method for efficiently obtaining a liquid sample from a gaseous sample and an electrostatic atomizer suitable for the method.

18 Claims, 17 Drawing Sheets

(51) Int. Cl.
*B05B 5/025* (2006.01)
*B05B 5/053* (2006.01)
*B05B 5/16* (2006.01)

(52) U.S. Cl.
CPC ............. *B05B 5/16* (2013.01); *G01N 1/2273* (2013.01); *G01N 33/497* (2013.01); *G01N 2001/2244* (2013.01); *G01N 2001/2282* (2013.01)

(56) References Cited

FOREIGN PATENT DOCUMENTS

| | | | |
|---|---|---|---|
| JP | 2013170964 | * | 9/2013 |
| JP | 2014-231047 | | 12/2014 |

* cited by examiner

APPARATUS AND METHOD FOR OBTAINING LIQUID SAMPLE FROM GASEOUS SAMPLE

BACKGROUND

1. Technical Field

The present invention relates to an electrostatic atomizer and a method for obtaining a liquid sample from a gaseous sample using the same.

2. Description of the Related Art

U.S. Pat. No. 7,972,277 discloses an exhaled breath analysis method using an electrostatic atomizer. FIG. 16 shows a cross-sectional view of an electrostatic atomizer 900 disclosed in U.S. Pat. No. 7,972,277. This electrostatic atomizer 900 comprises a container 901, an inlet 902, an outlet 903, a cooling part 904, an electrode part 905, an opposite electrode part 906, a chemical substance detecting part 907, a valve 908*a* and a valve 908*b*.

Japanese patent application laid-open publication No. 2014-231047A discloses an electrostatic atomizer. Japanese patent application laid-open publication No. 2007-333570A discloses a cell electrophysiological sensor and a method for measuring cell electrophysiological phenomenon using the same. FIG. 17 shows a cross-sectional view of the cell electrophysiological sensor disclosed in Japanese patent application laid-open publication No. 2007-333570A. This cell electrophysiological sensor comprises a well 91, a retention plate 92, a channel plate 93, a thin plate 94, a first through-hole 95, a second through-hole 96, a third through-hole 97, an inlet 99, an outlet 910, a first groove 913, and a second groove 914. According to the paragraph [0040] of Japanese patent application laid-open publication No. 2007-333570A, a first electrode (not shown) is provided in the well 91, and a second electrode (not shown) formed of silver chloride is provided in the first groove 913. Japanese patent application laid-open publication No. Hei 4-325080A discloses an amplifier of deoxyribonucleic acids and a method for amplifying deoxyribonucleic acids using the same. FIG. 18 shows a cross-sectional view of the amplifier disclosed in Japanese patent application laid-open publication No. Hei 4-325080A. This amplifier comprises a three-way valve 961, a three-way valve 962, a heat medium 921, a heat medium 922, a heat medium 923 and a capillary 991.

SUMMARY

The present invention provides an electrostatic atomizer comprising:
a container having an inlet;
an atomization electrode having one end projecting in the container;
an opposite electrode provided in the container;
a tubular collection electrode provided opposite to the atomization electrode;
a mask surrounding an outer periphery of the tubular collection electrode; and
a cooling part for cooling the tubular collection electrode, wherein
the opposite electrode is provided between the atomization electrode and the tubular collection electrode;
the mask is formed of resin;
the mask comprises a mask through-hole;
the tubular collection electrode is inserted in the mask through-hole; and
one end of the tubular collection electrode is located in the mask through-hole.

The present invention provides a method for obtaining a liquid sample from a gaseous sample using an electrostatic atomizer, the method comprising:
(a) preparing the electrostatic atomizer;
(b) supplying the liquid sample from the inlet to an inside of the container;
(c) applying a first voltage between the atomization electrode and the opposition electrode to generate charged fine particles from the gaseous sample; and
(d) collecting the charged fine particles as the liquid sample in the tubular collection electrode, while the tubular collection electrode is cooled using the cooling part.

The present invention provides a method for efficiently obtaining a liquid sample from a gaseous sample and an electrostatic atomizer suitable for the method.

DETAILED DESCRIPTION OF THE EMBODIMENT

Hereinafter, the embodiment of the present invention will be described with reference to the drawings.

First Embodiment

Electrostatic Atomizer 100

Figure 1:
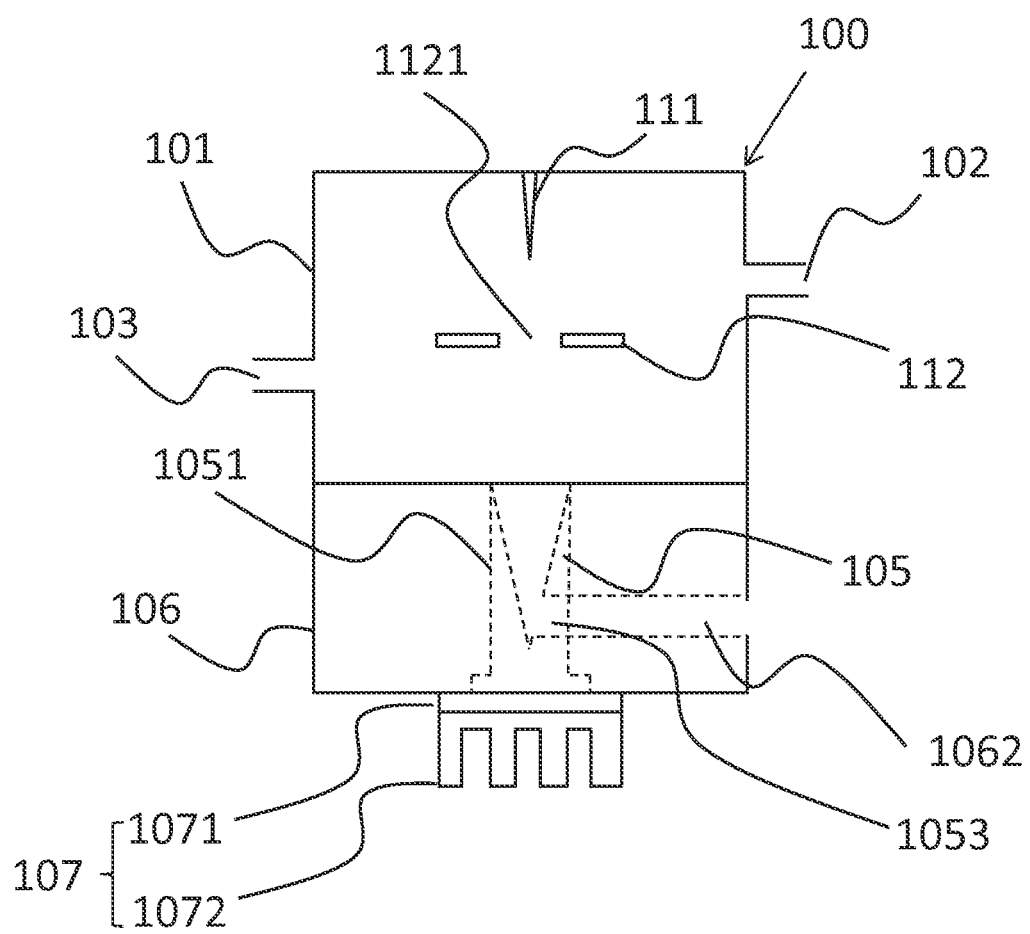
FIG. 1 shows a cross-sectional view of an electrostatic atomizer 100 according to a first embodiment.

FIG. 1 shows a cross-sectional view of an electrostatic atomizer 100 according to the first embodiment. The electrostatic atomizer 100 comprises a container 101 having an inlet 102, an atomization electrode 111 having one end projecting in the container 101, an opposite electrode 112 provided in the container 101, a tubular collection electrode 105 provided opposite to the atomization electrode 111, a mask 106 surrounding an outer periphery of the tubular collection electrode 105, and a cooling part 107 for cooling the tubular collection electrode 105.

See U.S. Pat. No. 7,972,277 for more detail of the container 101, the atomization electrode 111, and the opposite electrode 112. U.S. Pat. No. 7,972,277 is incorporated herein by reference.

Desirably, the container 101 is provided with an outlet 103. As is described later, a gaseous sample is supplied through the inlet 102 to the inside of the container 101. An excess of the gaseous sample is discharged through the outlet 103 to the outside of the container 101. As just described, the inlet 102 and the outlet 103 communicate with the inside of the container 101. An example of the gaseous sample is an exhaled breath or a room air. Another example of the gaseous sample is air in a car.

Figure 16:
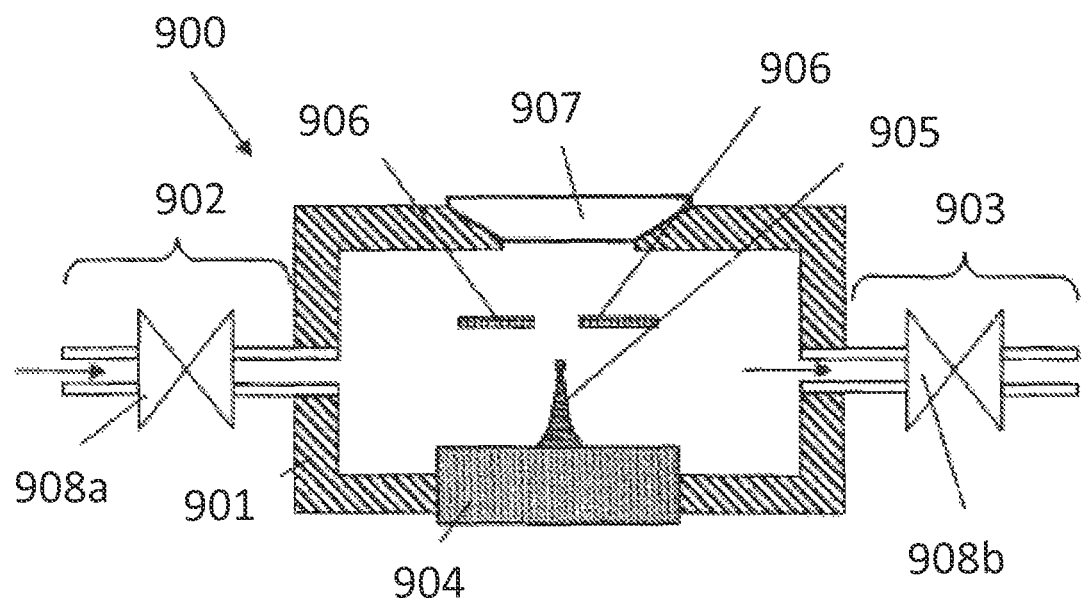
FIG. 16 shows a cross-sectional view of an electrostatic atomizer 900 disclosed in U.S. Pat. No. 7,972,277.
Figure 17:
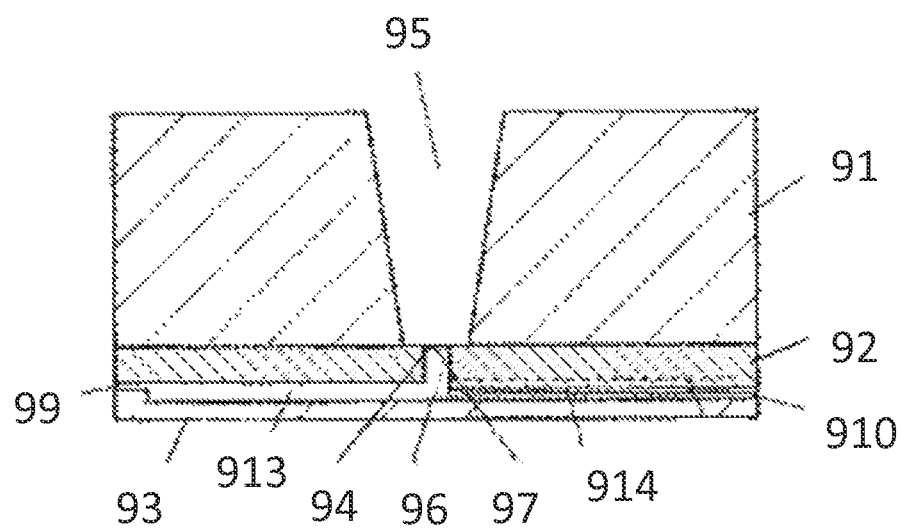
FIG. 17 shows a cross-sectional view of a cell electrophysiological sensor disclosed in Japanese patent application laid-open publication No. 2007-333570A.
Figure 18:
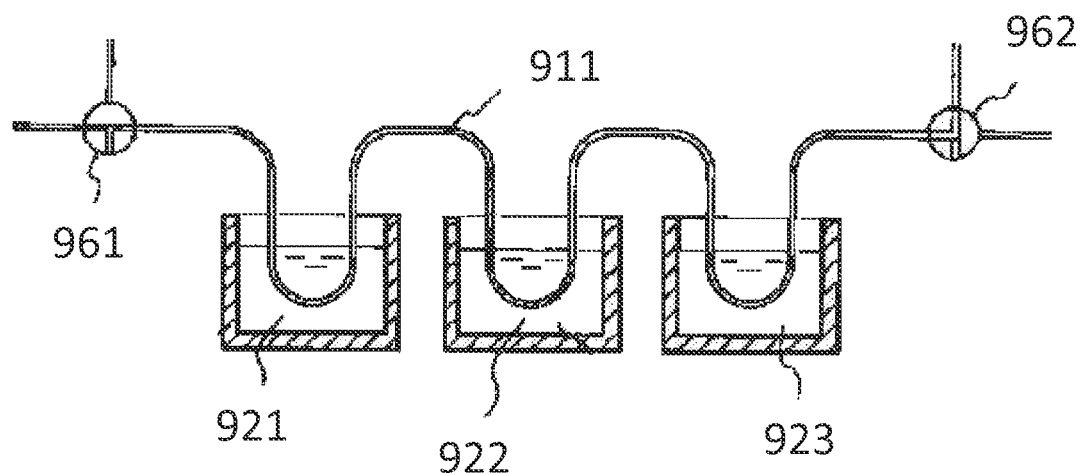
FIG. 18 shows a cross-sectional view of an amplifier disclosed in Japanese patent application laid-open publication No. Hei 4-325080A.

As shown in FIG. 1, it is desirable that the atomization electrode 111 has a shape of a needle. One end of the electrode 111 having a shape of a needle projects in the container 101. The other end of the atomization electrode 111 may be located in the container 101, as shown in FIG. 1. Alternatively, as shown in FIG. 16, the other end of the atomization electrode 111 (atomization electrode 905, in FIG. 16) may be located outside of the container 101.

It is desirable that the electrode 111 comprises a cooling device (not shown). The cooling device has an ability to cool the electrode 111.

The opposite electrode 112 is provided in the container 101. The opposite electrode 112 is provided between the atomization electrode 111 and the tubular collection electrode 105. It is desirable that the opposite electrode 112 has a shape of a ring such that a through-hole 1121 (hereinafter, referred to as "opposition electrode through-hole 1121") is formed just below the atomization electrode 111.

Figure 2:
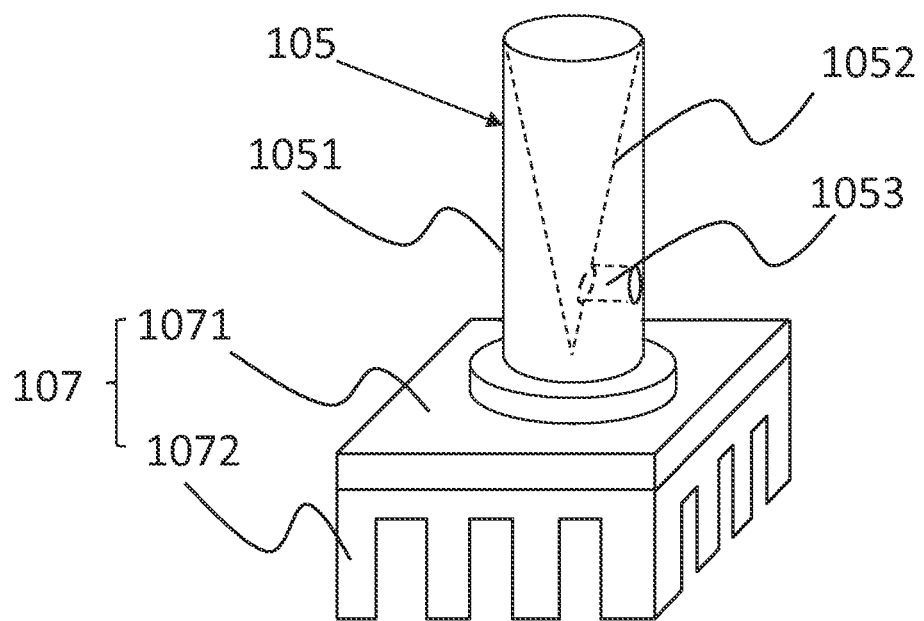
FIG. 2 shows an oblique view of a tubular collection electrode 105.

The tubular collection electrode 105 is provided so as to be located opposite to the atomization electrode 111. FIG. 2 shows an oblique view of the tubular collection electrode 105. The tubular collection electrode 105 has an outer periphery 1051 and an inner periphery 1052. In the method of the present invention, the liquid sample is formed as a droplet on the inner periphery 1052.

The tubular collection electrode 105 has one end (the upper end, in FIG. 2) and the other end (the lower end, in FIG. 2). The other end of the tubular collection electrode 105 is provided with a cooling part 107. The cooling part 107 comprises a Peltier element 1071 and a heat radiator 1072. The Peltier element 1071 is plate-like. The heat radiator 1072 is formed of aluminum. The plate-like Peltier element 1071 is interposed between the heat radiator 1072 and the tubular collection electrode 105. The cooling part 107 allows the tubular collection electrode 105 to be cooled.

The term used in the instant specification includes not only the meaning of "cylindrical" but also the meanings of "prismatic" and "ellipsoidal". In other words, a cross-section which appears when the tubular collection electrode 105 is cut along a plane perpendicular to the axial direction of the tubular collection electrode 105 may be circular, prismatic or ellipsoidal. Desirably, the cross-section is circular.

Figure 3:
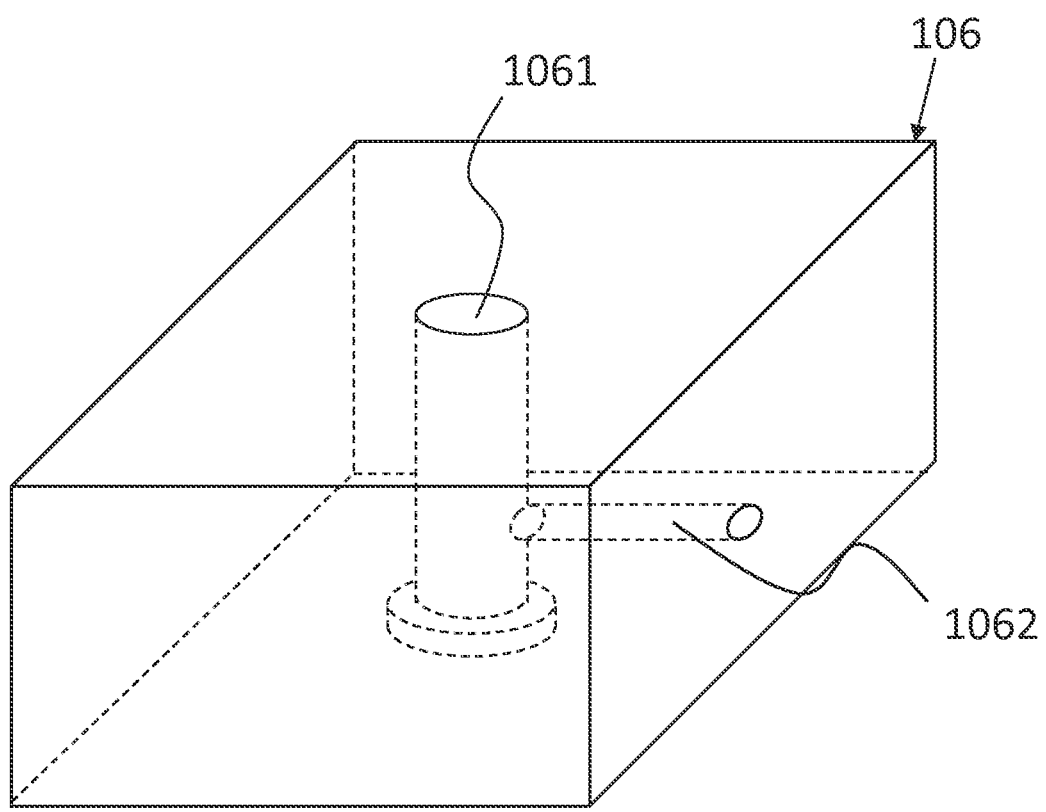
FIG. 3 shows an oblique view of a mask 106.

As shown in FIG. 1, a mask 106 is provided so as to surround the outer periphery 1051 of the tubular collection electrode 105. FIG. 3 shows an oblique view of the mask 106. As shown in FIG. 3, it is desirable that the mask 106 is plate-like. The mask 106 comprises a through-hole 1061 (hereinafter, referred to as "mask through-hole 1061") which penetrates the mask 106 along the thickness direction of the mask 106. The penetration direction of the mask through-hole 1061 is substantially parallel to the axial direction of the tubular collection electrode 105.

Figure 4:
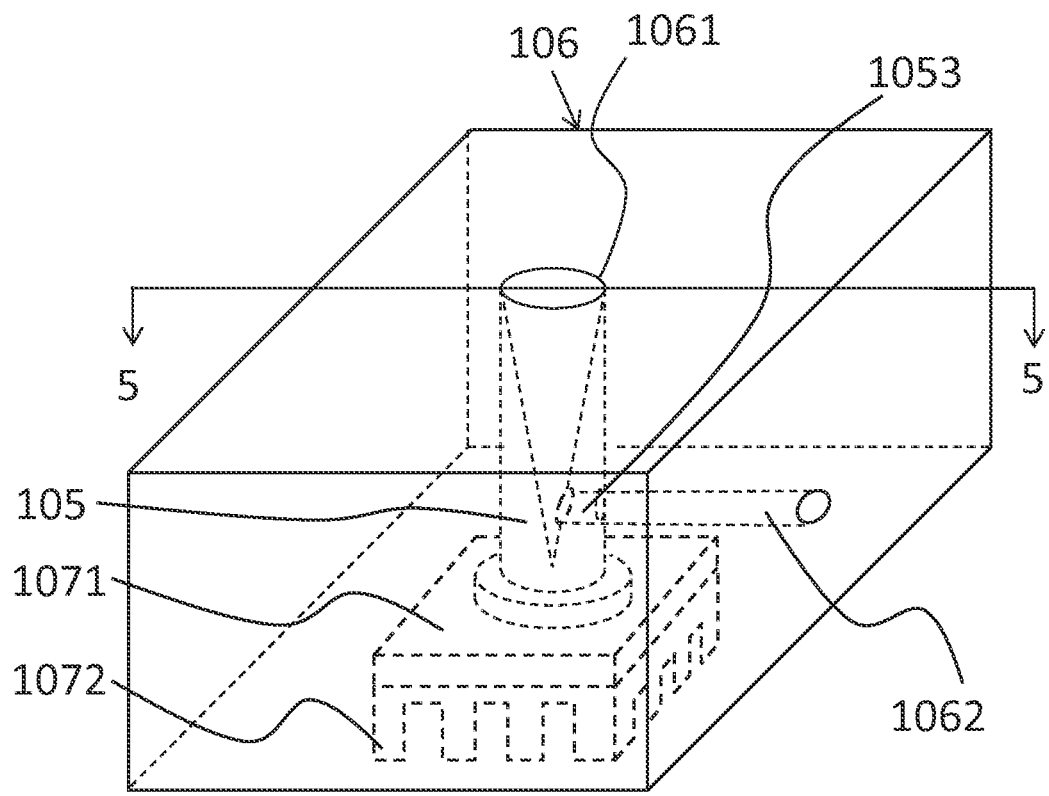
FIG. 4 shows an oblique view of the mask 106 in a situation where the tubular collection electrode 105 has been inserted in a mask through-hole 1061.

FIG. 4 shows an oblique view of the mask 106 in a situation where the tubular collection electrode 105 has been inserted in a mask through-hole 1061. As shown in FIG. 4, the tubular collection electrode 105 is inserted in the mask through-hole 1061. It is desirable that the outer periphery 1051 of the tubular collection electrode 105 is in contact with the inner periphery of the mask through-hole 1061.

The mask 106 is formed of resin. In case where the mask 106 is formed of metal, the liquid sample is not obtained at all. See the comparative example 2 which will be described later. The present inventor does not like to be bound to a theory; however, the reason why the liquid sample is not obtained at all in the comparative example 2 will be described below.

As is described later, in order to obtain the droplet as the liquid sample on the inner periphery 1052 of the tubular collection electrode 105, the tubular collection electrode 105 is cooled. However, metal has a high thermal conductivity, and the surface area of the mask 106 is much larger than the surface area of the inner periphery 1052 of the tubular collection electrode 105. For this reason, the droplet is hardly formed on the inner periphery 1052 of the tubular collection electrode 105. The droplet is formed on the mask 106 formed of metal. Therefore, in case where the mask 106 is formed of metal, the liquid sample is not obtained at all.

Figure 5:
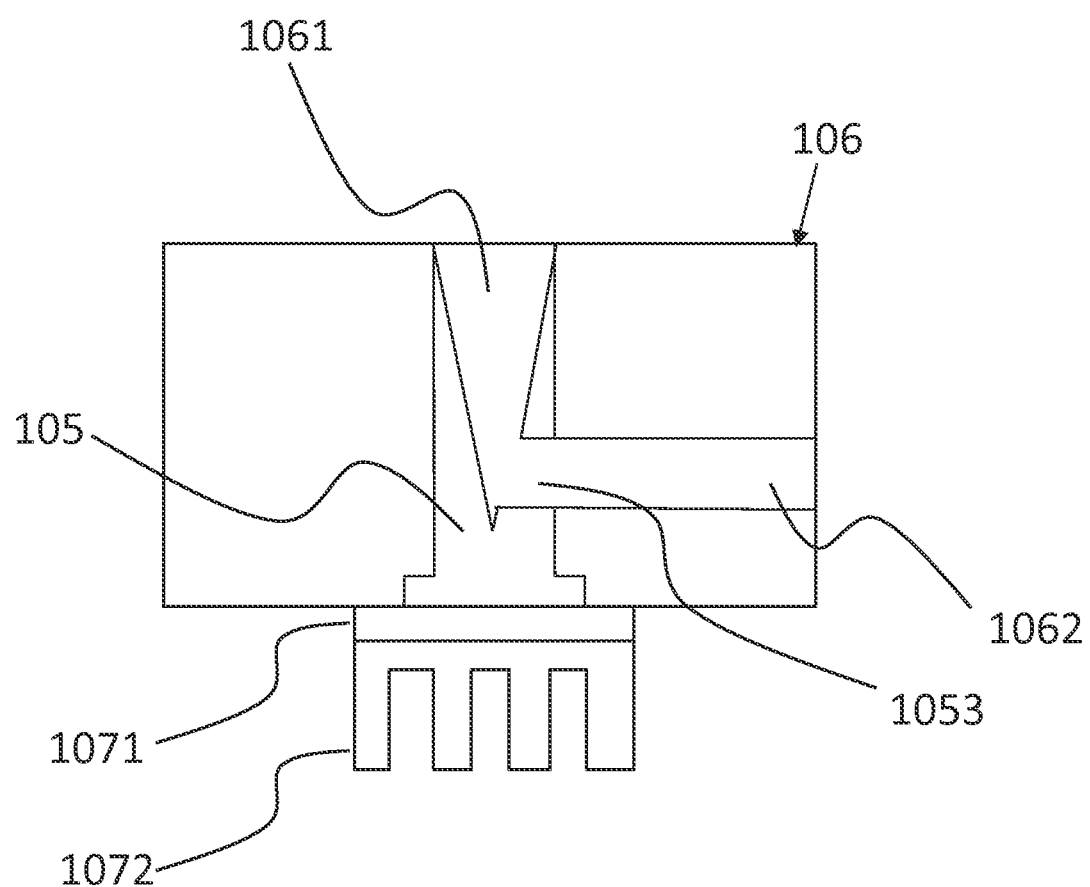
FIG. 5 shows a cross-sectional view taken along a 5-5 line included in FIG. 4.

FIG. 5 shows a cross-sectional view taken along an 5-5 line included in FIG. 4. As shown in FIG. 5, the one end (the upper end, in FIG. 4 and FIG. 5) of the tubular collection electrode 105 does not project from the upper end of the mask through-hole 1061. In other words, the one end of the tubular collection electrode 105 is located in the inside of the mask through-hole 1061.

Figure 6:
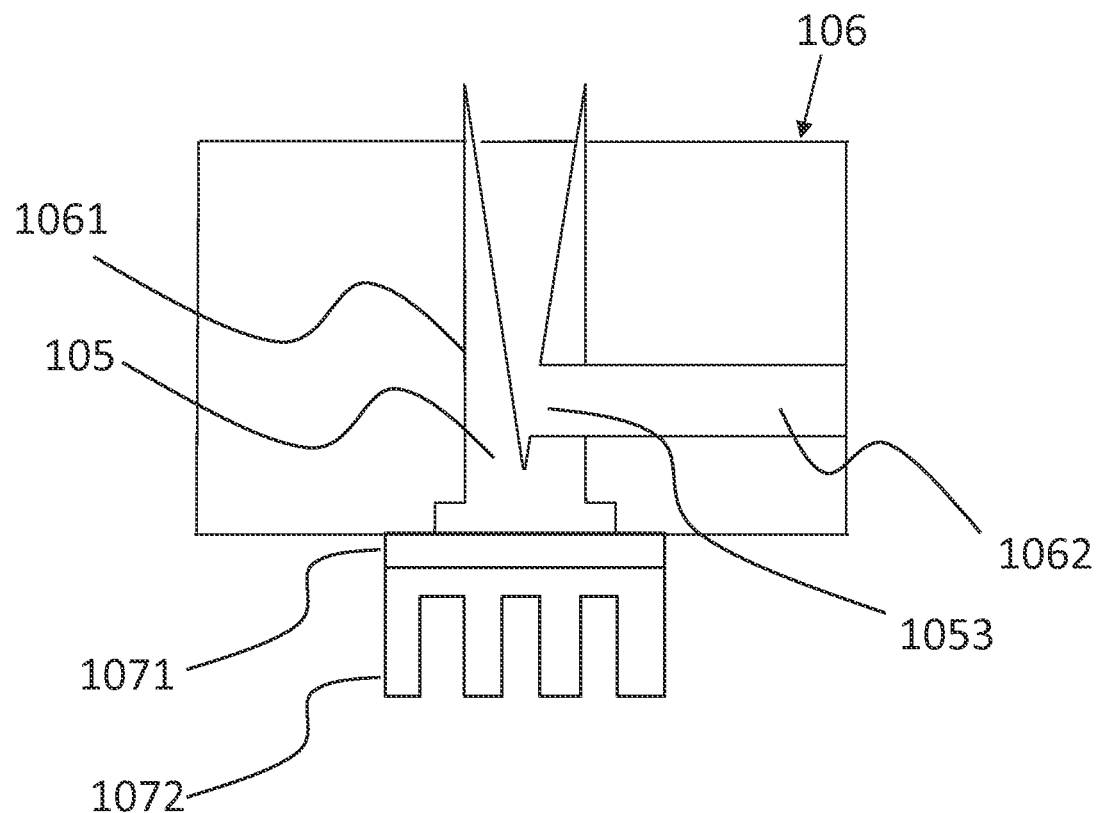
FIG. 6 shows a cross-sectional view in which the tubular collection electrode 105 projects from a top end of the mask through-hole 1061.

As shown in FIG. 6, the one end (the upper end, in FIG. 4 and FIG. 5) of the tubular collection electrode 105 must not project from the upper end of the mask through-hole 1061. This is because the droplet is formed as the liquid sample on a part of the outer periphery 1051 of the tubular collection electrode 105 which projects from the upper end of the mask through-hole 1061 in the case of FIG. 6. As a result, the droplet is not formed on the inner periphery 1052 of the tubular collection electrode 105.

(Method for Obtaining the Liquid Sample)

Hereinafter, a method for obtaining the liquid sample from the gaseous sample using the electrostatic atomizer 100 will be described below.

First, a user of the electrostatic atomizer 100 prepares the electrostatic atomizer 100. In other words, the user gets ready for the electrostatic atomizer 100.

The user supplies the gaseous sample through the inlet 102 to the inside of the container 101. Desirably, the sample is an exhaled breath. Desirably, the inside of the container 101 is filled with the gaseous sample.

Then, a first voltage is applied between the atomization electrode 111 and the opposite electrode 112. In this way, charged fine particles are generated from the gaseous sample in the container 101. As one example, the voltage is 3.7 volts. This first voltage may be increased with an increase in the distance between the electrode 111 and the opposite electrode 112. Needless to say, the first voltage may be decreased with a decrease in the distance between the electrode 111 and the opposite electrode 112. At the same time, the cooling part 107 cools the tubular collection electrode 105. The charged fine particles are collected as the droplet on the inner periphery 1052 of the cooled tubular collection electrode 105. In this way, the liquid sample is obtained on the inner periphery 1052 of the tubular collection electrode 105.

A second voltage may be applied between the opposite electrode 112 and the tubular collection electrode 105. If the second voltage is applied, a concentrated liquid sample is obtained on the inner periphery 1052 of the tubular collection electrode 105. In other words, in this case, the gaseous sample is concentrated as the liquid sample on the inner periphery 1052 of the tubular collection electrode 105. For more detail, see U.S. Pat. No. 7,972,277. If the second voltage is not applied, the gaseous sample is collected on the inner periphery 1052 as the liquid sample without being concentrated.

(Desirable Embodiment of the Tubular Collection Electrode 105 and the Mask 106)

As shown in FIG. 2, it is desirable that the inner periphery 1052 of the tubular collection electrode 105 has a shape of an inverted taper. In other words, it is desirable that the inner periphery 1052 has a shape of such an inverted taper that a cross-sectional area is decreased from the one end (the upper end, in FIG. 2) to the other end (the lower end, in FIG. 2) of the tubular collection electrode 105. As just described, it is desirable that a cavity surrounded by the inner periphery 1052 has a shape of an inverted circular cone, an inverted pyramid, or an inverted elliptical cone. It is more desirable that the cavity has a shape of an inverted circular cone. Due to such an inverse tapered shape, the droplet formed on the inner periphery 1052 collects spontaneously at the bottom of the tubular collection electrode 105. For this reason, it is easy to collect the droplet.

The droplet collected at the bottom of the inside of the tubular collection electrode 105 may be sucked using an aspirator such as a syringe or a pump. Alternatively, the droplet collected at the bottom of the inside of the tubular collection electrode 105 may be sucked as below.

As shown in FIG. 2, it is desirable that the tubular collection electrode 105 comprises a through-hole (hereinafter, referred to as "collection electrode through-hole 1053"). This collection electrode through-hole 1053 penetrates the tubular collection electrode 105 from the inner periphery 1052 to the outer periphery 1051. It is desirable that the penetration direction of the collection electrode through-hole 1053 is substantially perpendicular to the axial direction of the tubular collection electrode 105.

As shown in FIG. 3, the mask 106 has a pipe 1062. The pipe 1062 penetrates the mask 106 from the inner periphery of the mask through-hole 1061 to the outer periphery of the mask 106.

As shown in FIG. 4, when the tubular collection electrode 105 is inserted in the mask through-hole 1061, the collection electrode through-hole 1053 communicates with the pipe 1062. In other words, one long hole is formed of the collection electrode through-hole 1053 and the pipe 1062. It is desirable that the axial direction of the collection electrode through-hole 1053 is parallel to the axial direction of the pipe 1062.

Figure 7:
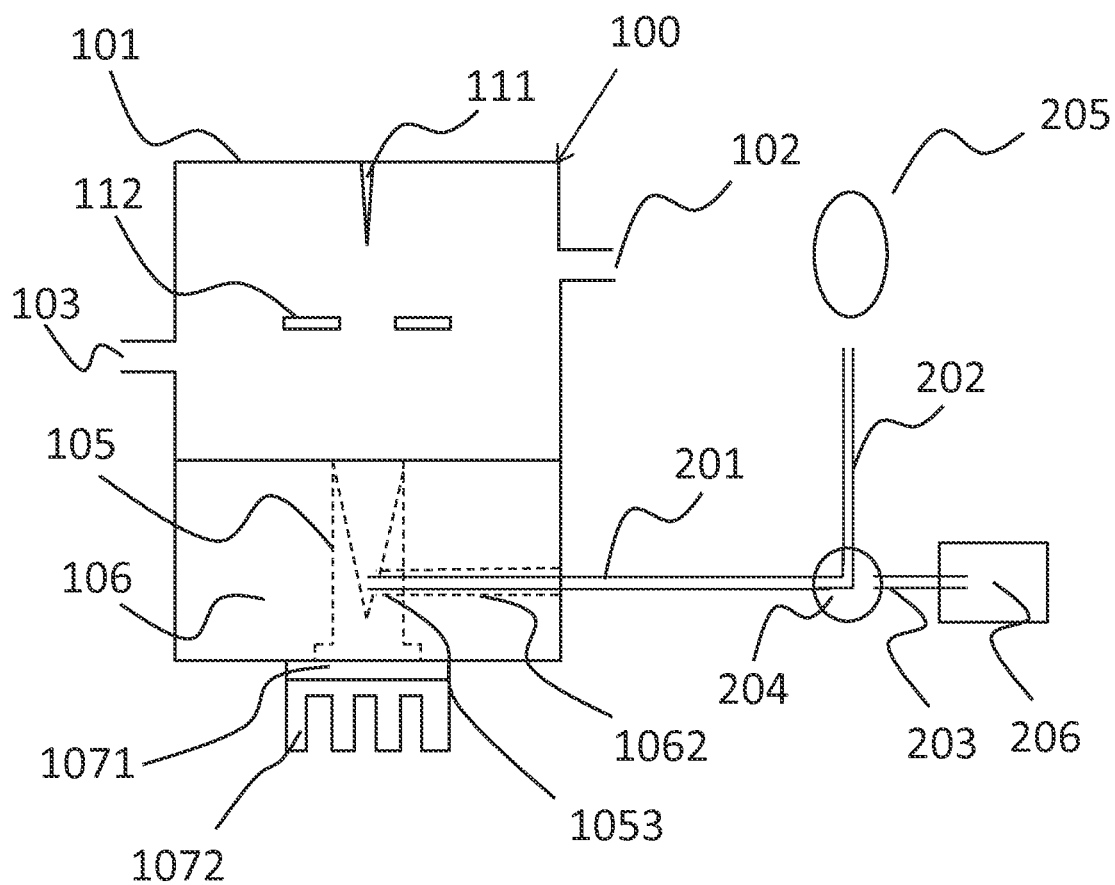
FIG. 7 shows a schematic view of the electrostatic atomizer 100 comprising a three-way valve and an analyzer.

FIG. 7 shows a schematic view of the electrostatic atomizer 100 comprising a three-way valve and an analyzer. As shown in FIG. 7, this electrostatic atomizer 100 comprises a first transport tube 201, a second transport tube 202, a third transport tube 203, a three-way valve 204 and an analyzer 206. It is desirable that each of the first transport tube 201, the second transport tube 202, and the third transport tube 203 is formed of a glass tube. In particular, it is desirable that the inner periphery of the first transport tube 201 is formed of glass. The first transport tube 201 has one end and the other end. The same goes for the second transport tube 202 and the third transport tube 203. As just described, it is desirable that each of the first transport tube 201, the second transport tube 202, and the third transport tube 203 is a capillary.

Figure 8:
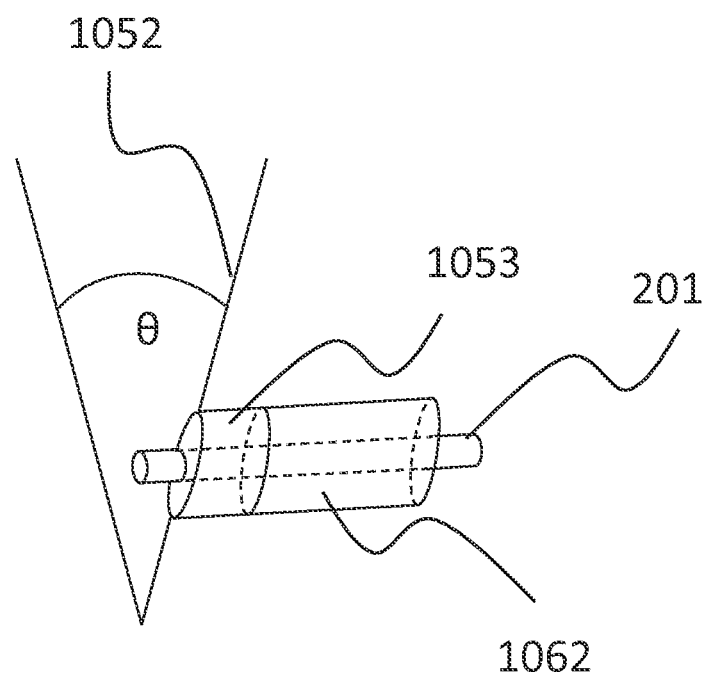
FIG. 8 shows an enlarged view of an end of a first transport tube 201.

FIG. 8 shows an enlarged view of the end (i.e., the other end) of the first transport tube 201. As shown in FIG. 7 and FIG. 8, the first transport tube 201 penetrates the pipe 1062 and the collection electrode through-hole 1053. In other words, the pipe 1062 and the collection electrode through-hole 1053 function as a sheath for the first transport tube 201.

The one end (the right end, in FIG. 7) of the first transport tube 201 is connected to the three-way valve 204. The one end (the lower end, in FIG. 7) of the second transport tube 202 is also connected to the three-way valve 204 again. The one end (the left end, in FIG. 7) of the third transport tube 203 is also connected to the three-way valve 204.

As shown in FIG. 7, the other end (the left end, in FIG. 7) of the first transport tube 201 is located in the cavity surrounded by the inner periphery 1052 having an inverse tapered shape. The cross-section of the cavity may be V-shaped. The other end (the upper end, in FIG. 7) of the second transport tube 202 may be provided with an aspirator 205. An example of the aspirator 205 is a pump, a dropper, or a syringe.

First, the other end (the upper end, in FIG. 7) of the second transport tube 202 is not provided with the aspirator 205. In other words, the other end (the upper end, in FIG. 7) of the second transport tube 202 is open. The three-way valve 204 is set so that the first transport tube 201 and the second transport tube 202 communicate with each other.

Figure 9:
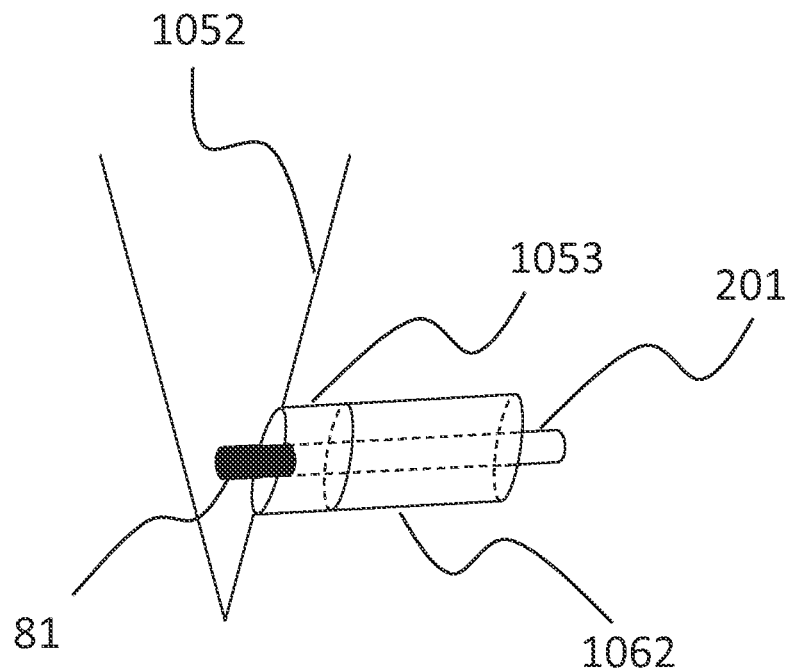
FIG. 9 shows how a liquid sample is sucked into the first transport tube 201 due to capillary action.

Then, the liquid sample is obtained in an above-mentioned way. In other words, the droplet is formed as the liquid sample on the inner periphery 1052 of the collection electrode 105. As shown in FIG. 9, the droplet is sucked into the first transport tube 201 as a first liquid 81.

Figure 10:
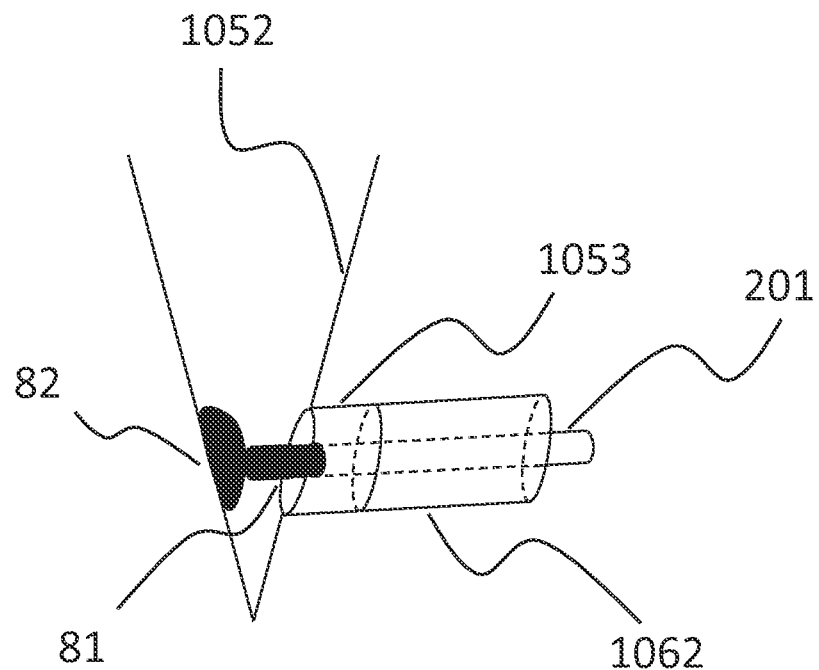
FIG. 10 shows how a liquid sample is sucked into the first transport tube 201 due to capillary action, subsequently to FIG. 9.
Figure 11:
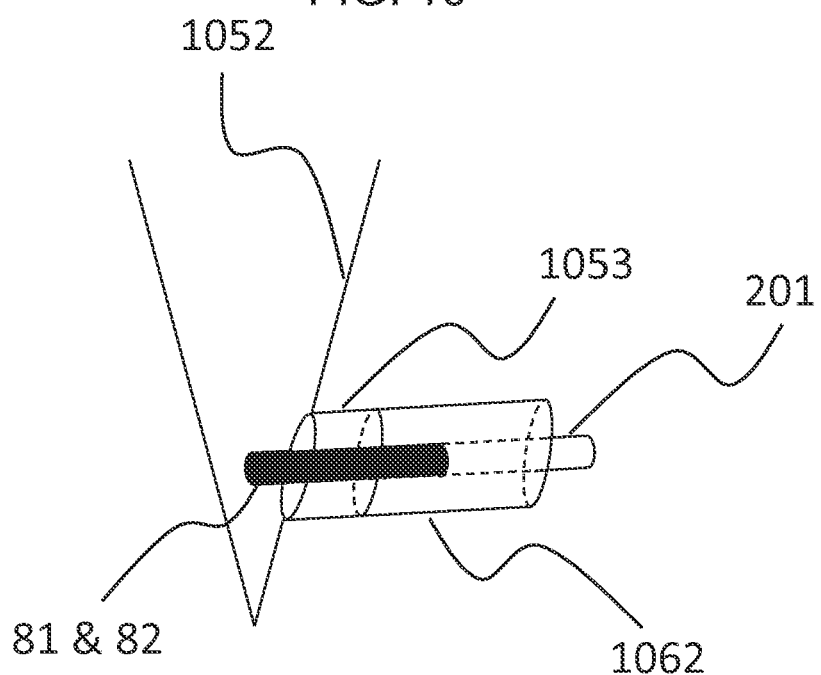
FIG. 11 shows how a liquid sample is sucked into the first transport tube 201 due to capillary action, subsequently to FIG. 10.

Continuously, the droplet is formed as the liquid sample on the inner periphery 1052 of the collection electrode 105. As shown in FIG. 10, this droplet will be sucked into the first transport tube 201 as the second liquid 82. As a result, as shown in FIG. 11, the first liquid 81 and the second liquid 82 are sucked continuously into the first transport tube 201 without interposing an air therebetween.

Figure 12:
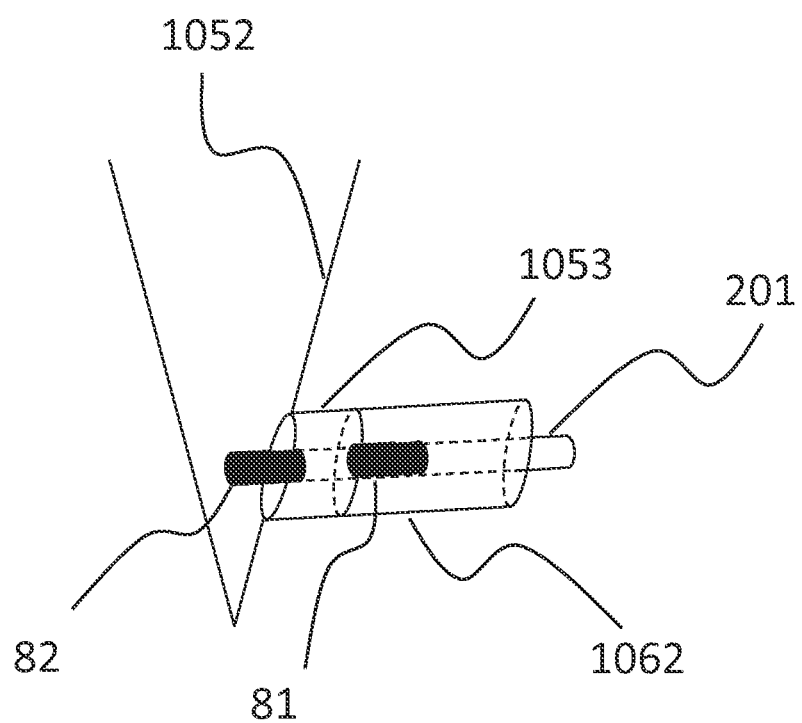
FIG. 12 shows how a liquid sample is undesirably sucked into the first transport tube 201 due to capillary action.

It is not desirable that the droplet is forced to be sucked into the first transport tube 201 from the other end thereof toward the one end thereof using an aspirator. This is because an air is interposed between the first liquid 81 and the second liquid 82 as shown in FIG. 12. The air prevents the volume of the droplet from being measured accurately.

Figure 13:
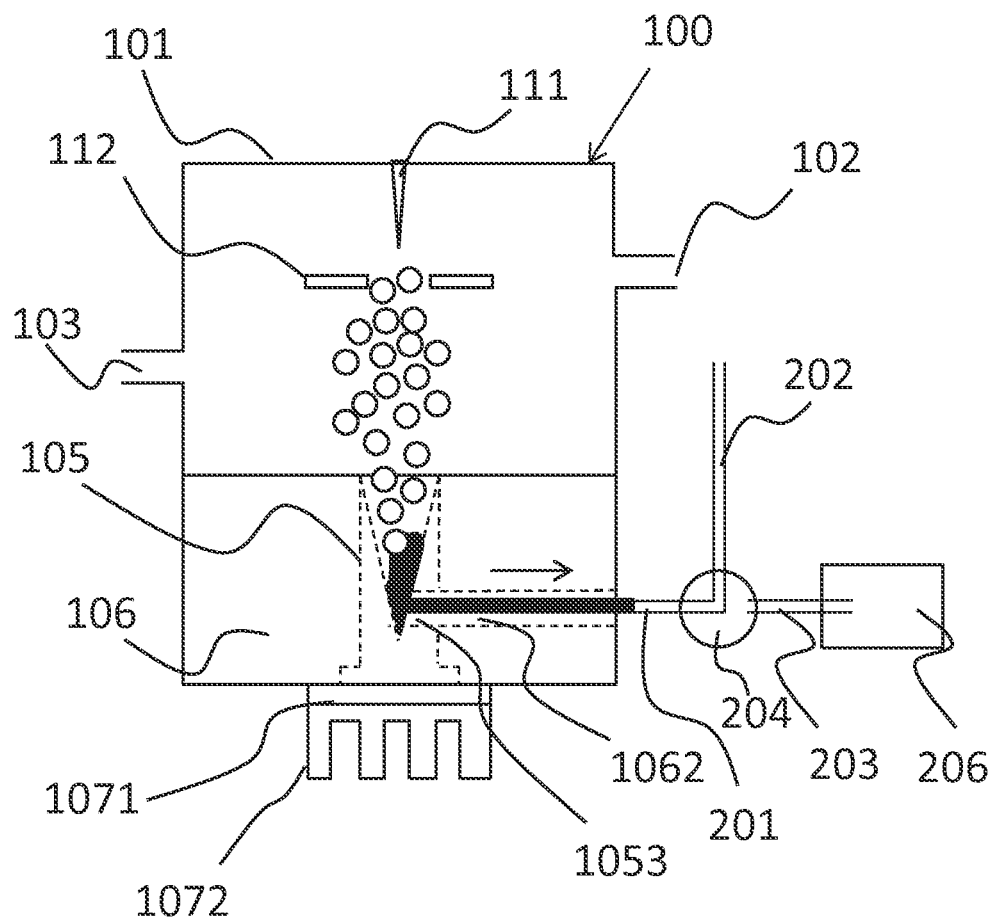
FIG. 13 shows a schematic view of the electrostatic atomizer 100 in which the liquid sample has been accumulated in the first transport tube 201 due to capillary action.

In this way, as shown in FIG. 13, the liquid sample is accumulated in the first transport tube 201 due to capillarly action.

Figure 14:
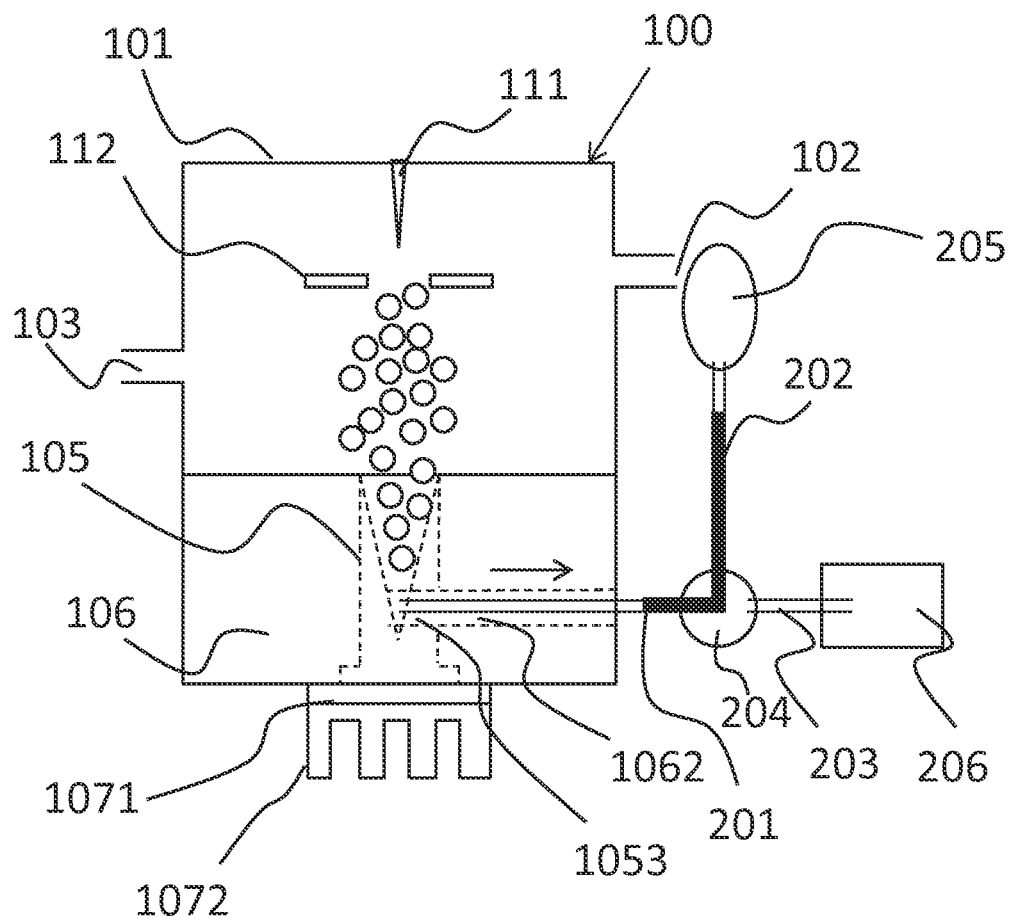
FIG. 14 shows a schematic view of the electrostatic atomizer 100 in which the liquid sample has been sucked in a second transport tube 202 due to capillary action.

Subsequently, as shown in FIG. 14, the other end (the upper end, in FIG. 7) of the second transport tube 202 is provided with the aspirator 205. Then, the liquid sample is sucked using the aspirator 205. In this way, the liquid sample reaches the inside of the second transport tube 202.

Figure 15:
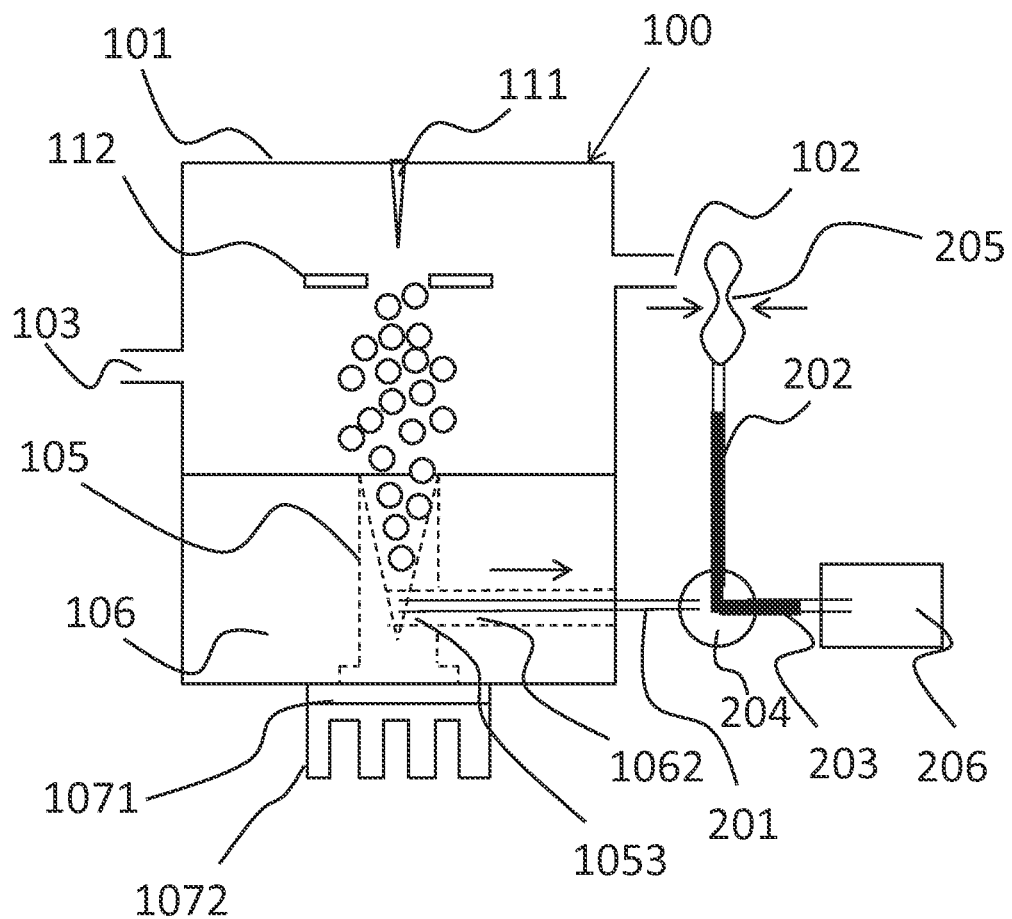
FIG. 15 shows a schematic view of the electrostatic atomizer 100 in which the liquid sample has been supplied to the analyzer 206 through a third transport tube 203.

Finally, as shown in FIG. 15, the three-way valve 204 is switched so as to communicate the second transport tube 202 and the third transport tube 203 with each other. Then, the liquid sample is pushed toward the inside of the third transport tube 203 using the aspirator 205. In this way, the liquid sample reaches the analyzer 206 for analyzing a chemical substance. The liquid sample is analyzed with the analyzer 206. In this way, the chemical substance contained in the gaseous sample is analyzed.

EXAMPLES

The present invention will be described in more detail with reference to the following examples.

Inventive Example 1

The electrostatic atomizer 100 shown in FIG. 1 was prepared. This electrostatic atomizer 100 comprised the container 101, the atomization electrode 111, the opposite electrode 112, the collection electrode 105, the mask 106 and the cooling part 107. The container 101 had the inlet 102 and the outlet 103. The container 101 contained the atomization electrode 111, the opposite electrode 112, the collection electrode 105, and the mask 106.

The container 101 was formed of acrylic plates each having a thickness of 3 millimeters. The container 101 had an inner dimension of 50 millimeters×50 millimeters×500 millimeters.

In a side view, the distance between the center of the inlet 102 and the upper surface of the container 101 was 5 millimeters. The distance between the center of the outlet 103 and the upper surface of the container 101 was also 5 millimeters. The inlet 102 and the outlet 103 were each formed of an stainless steel pipe having an outside diameter of ⅛ inch and an inside diameter of 1/16 inch.

An electrostatic atomization unit comprised the atomization electrode 111 and the opposite electrode 112. In the side view, the distance between the upper surface of the electrostatic atomization unit and the upper surface of the container 101 was 35 millimeters. The atomization electrode 111 was made of titanium. The atomization electrode 111 had a length of 2.5 millimeters and a diameter of 0.5 millimeters. In order to generate charged fine particles stably, one end (i.e., the lower end) of the atomization electrode 111 was provided with a metal ball having a diameter of 0.74 millimeters.

In the side view, the distance between the one end (i.e., the lower end) of the atomization electrode 111 and the opposite electrode 112 was 3 millimeters. The opposite electrode 112 had a shape of a ring having an outside diameter of 10 millimeters, an inside diameter of 3.5 millimeters, and a thickness of 0.5 millimeters. The opposite electrode 112 was formed of stainless steel.

The collection electrode 105 was formed of stainless steel. The collection electrode 105 comprised a cavity having an inverse tapered shape. The collection electrode 105 had the collection electrode through-hole 1053. The collection electrode 105 had an outside diameter of 4 millimeters and a height of 84 millimeters. The upper end of the cavity had a diameter of 3 millimeters. The cavity had a depth of 5.58 millimeters. As shown in FIG. 8, the angle θ formed by two inner peripheries 1052 which faced each other in the cross-sectional view was 30 degrees.

In the side view, the distance between the collection electrode through-hole 1053 and the upper end of the collection electrode 105 was 4.2 millimeters. The collection electrode through-hole 1053 had a diameter of 1/16 inch.

The mask 106 was formed of resin. The resin was polytetrafluoroethylene. The mask 106 comprised the mask through-hole 1061. The tubular collection electrode 105 was inserted in the mask through-hole 1061. The collection electrode through-hole 1053 communicated with the pipe 1062.

The Peltier element 1071 had a size of 15 millimeters×5 millimeters×4 millimeters. The Peltier element 1071 had a maximum endotherm of 5.6 W. The heat radiator 1072 was formed of aluminum.

As shown in FIG. 7 and FIG. 8, the first transport tube 201 was inserted so as to penetrate the pipe 1062 and the collection electrode through-hole 1053. The other end of the first transport tube 201 was located in the cavity of the collection electrode 105. Each of the first transport tube 201, the second transport tube 202, and the third transport tube 203 was a glass tube having an outside diameter of 1.60 millimeters and an inside diameter of 0.29 millimeters.

The liquid sample was obtained as below using such an electrostatic atomizer 100.

First, a gaseous sample heated to 45 degrees Celsius was supplied to the inside of the container 101 through the inlet at a rate of 500 milliliters/minute. The gaseous sample was air containing water vapor.

Then, a direct current voltage of 3.7 kV was applied between the atomization electrode 111 and the opposite electrode 112. The atomization electrode 111 and the opposite electrode 112 functioned as a cathode and an anode, respectively. The collection electrode 105 was cooled at the same time using the cooling part 107.

After the direct current voltage was applied, a water column having a shape of a circular cone was formed at the end of the atomization electrode 111. This water column may be referred to as a tailor corn. A large number of the charged fine particles were released from the tip of the water column.

In this way, the direct current voltage was applied for six minutes. Subsequently, the application of the direct current voltage was stopped.

The first transport tube 201 was withdrawn from the pipe 1062 and the collection electrode through-hole 1053. The amount of the liquid sample sucked into the first transport tube 201 by capillary action was measured based on a scale marked on the first transport tube 201.

This experiment was repeated five times. The following Table 1 shows the volume of the liquid sample sucked into the first transport tube 201.

TABLE 1

|  | Volume of Liquid Sample |
| --- | --- |
| First time | 1.34 microliters |
| Second time | 1.58 microliters |
| Third time | 1.55 microliters |
| Fourth time | 0.84 microliters |
| Fifth time | 1.50 microliters |

Comparative Example 1

In the comparative example 1, an experiment similar to the inventive example 1 was conducted, except that the mask 106 was not used.

The following Table 2 shows the volume of the liquid sample sucked into the first transport tube 201 in the comparative example 1. "0.00 microliters" means "off-scale low".

TABLE 2

|  | Volume of Liquid Sample |
| --- | --- |
| First time | 0.00 microliters |
| Second time | 0.00 microliters |
| Third time | 0.00 microliters |
| Fourth time | 0.00 microliters |
| Fifth time | 0.00 microliters |

As is clear from Table 1 and Table 2, the mask 106 allows the liquid sample to be obtained in the tubular collection electrode 105.

Comparative Example 2

In the comparative example 2, an experiment similar to the inventive example 1 was conducted, except that the mask 106 was formed of metal. Specifically, a metal wire was wound many times around the outer periphery 1051 of the tubular collection electrode 105. The thus-wound metal wire functioned as a disk-shaped metal mask 106.

The following Table 3 shows the volume of the liquid sample sucked into the first transport tube 201 in the comparative example 2.

TABLE 3

|  | Volume of Liquid Sample |
| --- | --- |
| First time | 0.00 microliters |
| Second time | 0.00 microliters |
| Third time | 0.00 microliters |
| Fourth time | 0.00 microliters |
| Fifth time | 0.00 microliters |

As is clear from Table 1 and Table 3, the mask 106 is required to be formed of resin. In the comparative example 2, the liquid sample was not formed in the tubular collection electrode 105. The liquid sample was formed on the surface of the metal mask 106.

INDUSTRIAL APPLICABILITY

The present invention can be used to analyze a chemical substance contained in a gas such as an exhaled breath, a room air, or an in-car air.

REFERENCE SIGNS LIST

100 Electrostatic atomizer
101 Container
102 Inlet
103 Outlet
111 Atomization electrode
112 Opposition electrode
1121 Opposition electrode through-hole
105 Tubular collection electrode
1051 Outer periphery
1052 Inner periphery
1053 Collection electrode through-hole
106 Mask
1061 Mask through-hole
1062 Pipe
107 Cooling part
1071 Peltier element
1072 Heat radiator

The invention claimed is:

1. An apparatus for obtaining a liquid sample from a gaseous sample, the apparatus comprising:
   a container having an inlet;
   an atomization electrode having one end projecting in the container;
   an opposite electrode provided in the container;
   a tubular collection electrode provided opposite to the atomization electrode;
   a covering block surrounding an outer periphery of the tubular collection electrode; and
   a cooling part for cooling the tubular collection electrode,
   wherein:
   the opposite electrode is provided between the atomization electrode and the tubular collection electrode,
   the covering block is a solid body formed of resin,
   the covering block comprises a covering block through-hole,
   the tubular collection electrode is inserted in the covering block through-hole, and
   one end of the tubular collection electrode is located in the covering block through-hole.

2. The apparatus according to claim 1, wherein the outer periphery of the tubular collection electrode is in contact with an inner periphery of the covering block through-hole.

3. The apparatus according to claim 1, wherein the tubular collection electrode has an inner periphery having a shape of an inverted taper such that a cross-sectional area thereof is decreased from the one end toward to the other end of the tubular collection electrode.

4. The apparatus according to claim 3, wherein the tubular collection electrode comprises a collection electrode through-hole which penetrates from the inner periphery to the outer periphery thereof.

5. The apparatus according to claim 4, wherein:
   the covering block comprises a pipe which penetrates from an inner periphery of the covering block through-hole to an outer periphery of the covering block, and
   the collection electrode through-hole communicates with the pipe.

6. The apparatus according to claim 5, further comprising:
   a first transport tube having one end and the other end;
   a second transport tube having one end and the other end;
   a third transport tube having one end and the other end; and
   a three-way valve, wherein:
   the first transport tube communicates with the collection electrode through-hole through the pipe, and
   the one ends of the first-third transport tubes are connected to the three-way valve.

7. The apparatus according to claim 6, wherein the other end of the second transport tube is provided with an aspirator.

8. The apparatus according to claim 6, wherein the other end of the third transport tube is provided with an analyzer for analyzing a chemical substance.

9. A method for obtaining a liquid sample from a gaseous sample using an apparatus, the method comprising:
(a) preparing the apparatus, wherein:
the apparatus comprises:
a container having an inlet;
an atomization electrode having one end projecting in the container;
an opposite electrode provided in the container;
a tubular collection electrode provided opposite to the atomization electrode;
a covering block surrounding an outer periphery of the tubular collection electrode; and
a cooling part for cooling the tubular collection electrode,
the opposite electrode is provided between the atomization electrode and the tubular collection electrode,
the covering block is a solid body formed of resin,
the covering block comprises a covering block through-hole,
the tubular collection electrode is inserted in the covering block through-hole, and
one end of the tubular collection electrode is located in the covering block through-hole;
(b) supplying the liquid sample from the inlet to an inside of the container;
(c) applying a first voltage between the atomization electrode and the opposition electrode to generate charged fine particles from the gaseous sample; and
(d) collecting the charged fine particles as the liquid sample in the tubular collection electrode, while the tubular collection electrode is cooled using the cooling part.

10. The method according to claim 9, wherein
in the step (d), a second voltage is applied between the opposite electrode and the tubular collection electrode to collect the liquid sample in which chemical substances contained in the gaseous sample have been concentrated.

11. The method according to claim 9, wherein
the outer periphery of the tubular collection electrode is in contact with an inner periphery of the covering block through-hole.

12. The method according to claim 9, wherein
the tubular collection electrode has an inner periphery having a shape of an inverted taper such that a cross-sectional area thereof is decreased from the one end toward to the other end of the tubular collection electrode.

13. The method according to claim 12, wherein
the tubular collection electrode comprises a collection electrode through-hole which penetrates from the inner periphery to the outer periphery thereof.

14. The method according to claim 13, wherein:
the covering block comprises a pipe which penetrates from an inner periphery of the covering block through-hole to an outer periphery of the covering block, and
the collection electrode through-hole communicates with the pipe.

15. The method according to claim 9, wherein:
the apparatus further comprises:
a first transport tube having one end and the other end;
a second transport tube having one end and the other end;
a third transport tube having one end and the other end; and
a three-way valve, wherein:
the tubular collection electrode comprises a collection electrode through-hole which penetrates from an inner periphery to an outer periphery thereof,
the covering block comprises a pipe which penetrates from an inner periphery of the covering block through-hole to an outer periphery of the covering block,
the collection electrode through-hole communicates with the pipe,
the other end of the third transport tube is provided with an analyzer for analyzing a chemical substance contained in the gaseous sample,
the first transport tube communicates with the collection electrode through-hole through the pipe, and
the one ends of the first-third transport tubes are connected to the three-way valve, and
the method further comprises:
(e) sucking the liquid sample collected in the tubular collection electrode in the step (d) into the second transport tube through the first transport tube and the three-way valve;
(f) communicating the second transport tube with the third transport tube using the three-way valve; and
(g) supplying the liquid sample sucked into the second transport tube in the step (e) to the analyzer through the third transport tube.

16. The method according to claim 15, wherein:
the first transport tube penetrates an inside of the collection electrode through-hole and an inside of the pipe,
the tubular collection electrode has an inner periphery having a shape of an inverted taper such that a cross-sectional area thereof is decreased from the one end toward to the other end of the tubular collection electrode, and
the other end of the first transport tube is located at a cavity surrounded by the inner periphery of the tubular collection electrode.

17. The method according to claim 15, wherein
the other end of the second transport tube is provided with an aspirator.

18. The method according to claim 9, wherein
the step (c) and the step (d) are conducted at the same time.

* * * * *